(12) United States Patent
Fleming et al.

(10) Patent No.: US 6,673,568 B1
(45) Date of Patent: Jan. 6, 2004

(54) METHOD AND APPARATUS FOR PROKARYOTIC AND EUKARYOTIC CELL QUANTITATION

(75) Inventors: James E. Fleming, Spokane, WA (US); Jason Buck Somes, Spokane, WA (US)

(73) Assignee: Genprime, Inc., Spokane, WA (US)

( * ) Notice: Subject to any disclaimer, the term of this patent is extended or adjusted under 35 U.S.C. 154(b) by 260 days.

(21) Appl. No.: 09/696,710

(22) Filed: Oct. 24, 2000

Related U.S. Application Data

(60) Provisional application No. 60/163,738, filed on Oct. 25, 1999.

(51) Int. Cl.$^7$ .................................................. C12Q 1/04

(52) U.S. Cl. ........................................ 435/34; 435/975

(58) Field of Search .......................... 435/4, 29, 34, 435/39, 6, 968, 975, 30, 31

(56) References Cited

U.S. PATENT DOCUMENTS

| | | | |
|---|---|---|---|
| 4,241,181 A | * 12/1980 | Lund .......................... | 435/34 |
| 4,242,447 A | 12/1980 | Findl et al. .................... | 435/39 |
| 4,288,539 A | 9/1981 | McAleer et al. ................ | 435/7 |
| 4,343,782 A | * 8/1982 | Shapiro ......................... | 424/3 |
| 4,544,546 A | 10/1985 | Wang et al. .................... | 424/7.1 |
| 4,710,472 A | * 12/1987 | Saur et al. ..................... | 435/287 |
| 4,859,584 A | * 8/1989 | Horan et al. ................... | 435/29 |
| 5,057,413 A | 10/1991 | Terstappen et al. ............. | 435/6 |
| 5,436,134 A | 7/1995 | Haugland et al. .............. | 435/34 |
| 5,437,980 A | 8/1995 | Haugland ...................... | 435/6 |
| 5,534,416 A | * 7/1996 | Millard et al. ................. | 436/34 |
| 5,545,535 A | * 8/1996 | Roth et al. ..................... | 435/34 |
| 5,563,070 A | 10/1996 | Yamamoto et al. ............ | 436/63 |
| 5,582,984 A | 12/1996 | Bieniarz et al. ................ | 435/6 |
| 5,656,449 A | * 8/1997 | Yue .............................. | 435/34 |
| 5,658,751 A | * 8/1997 | Yue et al. ...................... | 435/34 |
| 5,695,946 A | 12/1997 | Benjamin et al. .......... | 435/7.32 |
| 5,734,058 A | 3/1998 | Lee .............................. | 546/176 |
| 5,798,115 A | * 8/1998 | Santerre et al. | |
| 5,804,448 A | 9/1998 | Wang et al. .................... | 436/63 |
| 5,888,736 A | 3/1999 | Lacroix et al. ................. | 435/6 |
| 5,939,282 A | 8/1999 | Harman et al. ................ | 435/29 |
| 5,968,762 A | 10/1999 | Jadamec et al. ............... | 435/18 |
| 5,994,067 A | 11/1999 | Wood et al. .................... | 435/6 |
| 6,312,896 B1 | * 11/2001 | Heroux et al. ................. | 435/6 |
| 6,455,271 B1 | * 9/2002 | Little, II et al. ............... | 435/29 |

FOREIGN PATENT DOCUMENTS

| | | |
|---|---|---|
| DE | 19832007 A1 | 1/2000 |
| GB | 1503828 | 3/1978 |
| WO | WO 97/17463 | 5/1997 |
| WO | WO 99/35288 | * 7/1999 |

OTHER PUBLICATIONS

Haugland, R. Handbook of Fluorescent Probes and Research Chemical, Molecular Probes. 1996 6th Ed., pp. 4, 149–150, 161–162.*

Frankfurt O. Flow Cytometric Measurement of Cell Viability Using DNase Exclusion. Methods in Cell Biology 33:13–18, 1990.*

Tatton N. A Fluorescent Double Labeling Method to Detect and Confirm Apoptotic Nuclei in Parkinson's Disease. Annals of Neurology 44(3 Suppl 1) S142–S148, Sep. 1998.*

Derwent abstract of DE 19724781A1 (Acc No 1999–082269). Batel et al. (1998). Determining DNA damage and repair—using PicoGreen, a fluorescing dye which binds specifically to double stranded DNA but not to single stranded DNA.*

English Abstract of DE 19832007 A1, esp@cenet, Jan. 27, 2000.

Caron et al., "Assessment of bacterial viability status by flow cytometry and single cell sorting," *Journal of Applied Microbiology* 84: 988–998, 1998.

Emaus et al., "Rhodamine 123 as a probe of transmembrane potential in isolated rat–liver mitochondria: spectral and metabolic properties," *Biochimica et Biophysica Acta* 850: 436–448, 1986.

Rundquist et al., "Cytofluorometric Quantitation of Acridine Orange Uptake by Cultured Cells," *Acta Pathologica Microbiol. Immunol. Scand. Sect. A* 92: 303–309, 1984.

Catt et al., "Hoechst staining and exposure to UV laser during flow cytometric sorting does not affect the frequency of detected endogenous DNA nicks in abnormal and normal human spermatozoa," *Molecular Human Reproduction* 821–825, 1997.

Latt and Wohlleb, "Optical Studies of the Interaction of 33258 Hoechst with DNA, Chromatin, and Metaphase Chromosomes," *Chromosoma* 52(4): 297–316, 1975.

Ferguson and Denny, "Microbial mutagenic effects of the DNA minor groove binder pibenzimol (Hoechst 33258) and a series of mustard analogues," *Mutation Research* 329(1): 19–27, 1995.

Griffith et al., "An evaluation of luminometry as a technique in food microbiology and a comparison of six commercially available luminometers," *Food Science and Technology Today* 8(4): 209–216, 1994.

Singer et al., "Characterization of PicoGreen Reagent and Development of a Fluorescence–Based Solution Assay for Double–Stranded DNA Quantitation," *Analytical Biochemistry* 249: 228–238, 1997.

(List continued on next page.)

*Primary Examiner*—Ralph Gitomer
(74) *Attorney, Agent, or Firm*—Seed Intellectual Property Law Group PLLC

(57) ABSTRACT

This invention describes kits for quantifying viable cells in a sample using fluorescent dyes that can be internalized predominately by viable cells and have fluorescence properties measurably altered when bound to target components. These kits circumvent the need for training personnel in plating, growing and count viable cells, and reduce both the time and the cost required for cellular quantitation according to existing techniques.

4 Claims, 2 Drawing Sheets

OTHER PUBLICATIONS

Singer et al., *Biotechnology International*, Connor and Fox (eds.), Universal Medical Press, Inc., 1997, "Sensitive Fluorescent Stains for Detecting Nucleic Acids in Gels and Solutions," pp. 267–277.

Singhal et al., "DNA–Protein Interactions and Separation of Restriction Fragments by Capillary Electrophoresis," *The FASEB Journal* 9(6): A1423, Abstract No. 965, Apr. 24 1995.

Suzuki et al., "Fluorescence Counter–Staining of Cell Nuclear DNA for Multi–Color Laser Confocal Microscopy," *Acta. Histochem. Cytochem.* 31(4): 297–301, 1998.

Tranvik, L.J., "Rapid fluorometric assay of bacterial density in lake water and seawater," *Limnol. Oceanogr.* 42(7): 1629–1634, 1997.

Veldhuis et al., "Cellular DNA Content of Marine Phytoplankton Using Two New Fluorochromes: Taxonomic and Ecological Implications," *J. Phycol.* 33: 527–541, 1997.

Yan et al., "Characteristics of Different Nucleic Acid Staining Dyes for DNA Fragment Sizing by Flow Cytometry," *Anal. Chem.* 71(24): 5470–5480, Dec. 15, 1999.

Zhu et al., "Cell cycle–dependent modulation of telomerase activity in tumor cells," *Proc. Natl. Acad. Sci. USA* 93: 6091–6095, Jun. 1996.

Moran et al., "Nonelectrophoretic Genotyping Using Allele–Specific PCR and a dsDNA–Specific Dye," *BioTechniques* 24: 206–212, Feb. 1998.

Murakami et al., "Quantitation of Adenovirus DNA and Virus Particles with the PicoGreen Fluorescent Dye," *Analytical Biochemistry* 274: 283–288, 1999.

Niemeyer et al., "Fluorometric Polymerase Chain Reaction (PCR) Enzyme–Linked Immunosorbent Assay for Quantification of Immuno–PCR Products in Microplates," *Analytical Biochemistry* 246: 140–145, 1997.

Papadimitriou and Lelkes, "Measurement of cell numbers in microtiter culture plates using the fluorescent dye Hoechst 33258," *Journal of Immunological Methods* 162: 41–45, 1993.

Parpais et al., "Effect of phosphorus starvation on the cell cycle of the photosynthetic prokaryote *Prochlorococcus* spp.," *Marine Ecology Progress Series* 132: 265–274, Feb. 29, 1996.

Pinder et al., *New Techniques in Food and Beverage Microbiology*, Kroll et al. (eds.), Blackwell Scientific Publications, 1993, chapter 6, "Detection and Enumeration of Viable Bacteria by Flow Cytometry," pp. 67–86.

Rago et al., "DNA Fluorometric Assay in 96–Well Tissue Culture Plates Using Hoechst 33258 after Cell Lysis by Freezing in Distilled Water," *Analytical Biochemistry* 191: 31–34, 1990.

Romppanen et al., "Optimal Use of the Fluorescent PicoGreen Dye for Quantitative Analysis of Amplified Polymerase Chain Reaction Products on Microplate," *Analytical Biochemistry* 279: 111–114, Mar. 2000.

Seville et al., "Fluorometric Assay for DNA Polymerases and Reverse Transcriptase," *BioTechniques* 21(4): 664–672, Oct. 1996.

Enger, Ø., "Use of the Fluorescent Dye PicoGreen™ for Quantification of PCR Products after Agarose Gel Electrophoresis," *BioTechniques* 21(3): 372–374, Sep. 1996.

Ferrari et al., "Analytical Methods for the Characterization of Cationic Lipid–Nucleic Acid Complexes," *Human Gene Therapy* 9: 341–351, Feb. 10, 1998.

Hall et al., "An Approach to High–throughput Genotyping," *Genome Research* 6: 781–790, 1996.

Haugland, R.P., *Handbook of Fluorescent Probes and Research Chemicals*, Spence, M. (ed.), Molecular Probes, Eugene, OR, 1996, "PicoGreen dsDNA Quantitation Reagent," p. 162.

Holst et al., "Allosteric modulation of AMPA–type glutamate receptors increases activity of the promoter for the neural cell adhesion molecule, N–CAM," *Proc. Natl. Acad. Sci. USA* 95: 2597–2602, Mar. 1998.

Hopwood et al., "Rapid Quantification of DNA Samples Extracted from Buccal Scrapes Prior to DNA Profiling," *BioTechniques* 23: 18–20, Jul. 1997.

Mansfield et al., "Nucleic acid detection using non–radioactive labeling methods," *Molecular and Cellular Probes* 9: 145–156, 1995.

Marie et al., "Application of the Novel Nucleic Acid Dyes YOYO–1, YO–PRO–1, and PicoGreen for Flow Cytometric Analysis of Marine Prokaryotes," *Applied and Environmental Microbiology* 62(5): 1649–1655, May 1996.

Matsuzaki et al., "Nuclear Staining for Laser Confocal Microscopy," *Acta Histochem. Cytochem.* 30(3): 309–314, 1997.

Ahn et al., "PicoGreen quantitation of DNA: effective evaluation of samples pre– or post– PCR," *Nucleic Acids Research* 24(13): 2623–2625, 1996.

Blaheta et al., "Development of an ultrasensitive in vitro assay to monitor growth of primary cell cultures with reduced mitotic activity," *Journal of Immunological Methods* 211: 159–169, 1998.

Bolger et al., "Fluorescent Dye Assay for Detection of DNA in Recombinant Protein Products," *BioTechniques* 23(3): 532–536, 1997.

Chadwick et al., "Heterozygote and Mutation Detection by Direct Automated Fluorescent DNA Sequencing Using a Mutant Taq DNA Polymerase," *BioTechniques* 20(4): 676–683, Apr. 1996.

\* cited by examiner

TBAK Correlation Chart for Redi-Set Mesophilic Bacteria

| TBAK Reading | Colony Forming Units/ml |
|---|---|
| 15000 | $6.0 \times 10^8$ |
| 13500 | $5.4 \times 10^8$ |
| 12000 | $4.8 \times 10^8$ |
| 10000 | $4.2 \times 10^8$ |
| 8500 | $3.6 \times 10^8$ |
| 7000 | $3.0 \times 10^8$ |
| 5500 | $2.4 \times 10^8$ |
| 3500 | $1.8 \times 10^8$ |
| 2000 | $1.2 \times 10^8$ |

Fig. 1

METHOD AND APPARATUS FOR PROKARYOTIC AND EUKARYOTIC CELL QUANTITATION

CROSS REFERENCE TO RELATED APPLICATIONS

The present application claims priority to U.S. Provisional Application No. 60/163,738, filed on Oct. 25, 1999.

TECHNICAL FIELD

The present invention relates generally to methods for the rapid quantitation of cells. More specifically, the present invention involves staining viable cells in a sample with a fluorescent dye and measuring the fluorescence.

BACKGROUND OF THE INVENTION

The ability to quantify viable cells is vitally important to the food, pharmaceutical, environmental, manufacturing and clinical industries. Several methods are currently employed for the quantitation of viable cells. These methods include, but are not limited to, the standard plate count, dye reduction and exclusion methods, electrometric techniques, microscopy, flow cytometry, bioluminescence, and turbidity.

The standard plate count allows the enumeration of viable cells (or clumps of cells) also known as colony forming units (cfu) when the cells are grown on the appropriate medium under growth conditions. Atlas, R. M. and Bartha, R., *Microbial Ecology*, Addison Wesley Longman, New York, (1998). Current standards of live organism counts are based on the standard plate count, particularly in the food industry. However, colony counts are difficult to interpret since bacteria often clump or form chains that can give rise to significantly inaccurate estimations of the total number of live organisms in a sample. Also, bacteria, for example, can be in a "metabolically damaged" state and not form countable colonies on a given medium. This is a greater problem when selective media are used. Thus, the standard plate count does not provide a definitive count of viable cells in a sample. Given these factors, such testing also requires skilled technicians who can distinguish separate cfus and who can aid in selecting appropriate growth medium. Moreover, the technique is not useful when rapid determination of cell counts is required since it often requires over 24 hours to obtain plate count results.

Dye reduction methods rely on the cell of interest to oxidize or reduce a particular dye. Harrington, W. F., (1998) *Laboratory Methods in Food Microbiology*, Academic Press, San Diego. These methods measure the activity of metabolically active organisms rather than provide an accurate measure of the total number of viable cells in a sample. Dyes, such as methylene blue, coupled with microscopic counting, are routinely employed to determine the relative number of microorganisms. This technique is widely employed but nevertheless suffers from factors that must be held constant during the assay, i.e., medium used, chemical conditions, temperature and the types of cells being examined. Also, dye reduction tests that incorporate microscopic counting techniques require trained technical personnel and often depend upon subjective interpretations.

Dye exclusion methods of cell quantitation depend on the ability of living cells to pump dye out of the cell and into the surrounding fluid medium. While dye may enter the interior of both live and dead cells, dead cells are not capable of actively pumping the dye out under the conditions and methods normally used. Dye exclusion is commonly used to enumerate animal, fungal and yeast cells. It is a method requiring skill, correct timing and correct choice of dye. It is not applicable to certain microbes and it yields incorrect live counts with stressed cells.

Electrometric methods such as impedance measurement indirectly determine the number of viable cells by measuring changes in the conductance of the growth medium following a period of cell growth. Stannard, C. J., Pettit, S. B., Skinner, F. A. (1989) *Rapid Microbiological Methods for Foods, Beverages and Pharmaceuticals* (ed. C. J. Stannard, S. B. Pettit and F. A. Skinner) Oxford: Blackwell Scientific. They are rapid tests that depend on variables that must be held constant and require expensive instrumentation. The Bactometer, by bioMerieux (France), is an example of an impedance instrument system designed for making estimates of viable cells in a sample.

Microscopic techniques typically involve counting a dilution of cells on a calibrated microscopic grid, such as a hemocytometer. A recent improvement in this technique is the direct epifluorescent filter technique (DEFT). Pettipher, G. L., Kroll, R. G. Farr, L. J. (1989) *Rapid Microbiological Methods for Foods, Beverages and Pharmaceuticals* (ed. C. J. Stannard, S. B. Pettit and F. A. Skinner) Oxford: Blackwell Scientific. In this technique, samples are filtered through a membrane filter that traps the cells to be counted. A fluorescent dye is attached to the cells and they are illuminated with ultraviolet light and counted. The technique requires an expensive microscope (an epifluorescent instrument) and a trained individual or an expensive automated system.

Flow cytometry involves the differential fluorescent staining of cells suspended in a relatively clear fluid stream of relatively low viscosity. The cell suspension is mixed with the fluorescent dye and illuminated in a flow cell by a laser or other light source. Labeled cells are detected automatically by a fluorescence detector focused on the cell. Brailsford, M. A. and Gatley, S. (1993) *New Techniques in Food and Beverage Microbiology* (ed. R. G. Kroll, A. Gilmour and M. Sussman Oxford: Blackwell Scientific. Pinder, A. C., Edwards, C. Clarke, R. G. (1993) *New Techniques in Food and Beverage Microbiology* (ed . R. G. Kroll. A. Gilmour and M. Sussman Oxford: Blackwell Scientific. The technique requires, and is limited by, expensive equipment. Some flow cytometric devices have been used by the food and dairy industry, but their application is limited by the high cost of instrumentation.

Bioluminescence has been routinely employed in the food sanitation industry to detect and quantify live organisms and cells. A common method employs the use of luciferin-luciferase to detect the presence of ATP. Harrington, W. F., (1998) *Laboratory Methods in Food Microbiology*, Academic Press, San Diego. Griffith. C. J., Blucher, A., Fleri, J. (1994) *Food Science and Technology Today* 8: 209–216. When used to quantitate cells, the technique depends on the assumption that there is a constant amount of ATP in a viable cell. ATP levels vary in a single cell over more than two orders of magnitude, making this method a relatively inaccurate technique for the enumeration of live organisms in a sample.

Turbidity of a liquid sample can be measured as an indication of the concentration of cells due to the light scattering/absorbing qualities of suspended cells. Harrington, W. F., (1998) *Laboratory Methods in Food Microbiology*, Academic Press, San Diego. The method is old but is still employed to estimate the bacterial concentration in a sample. The method is rapid and simple but is highly inaccurate since all cells, particles and substances, including non-living particulate matter, interfere with the interpretation of the results. Thus, while extremely beneficial under laboratory growth conditions where only one particular species is in the sample, it is usually not used for quantifying cells in a sample with multiple particulate species.

The present invention for the quantitation of cells is designed to overcome at least three problems that have been identified within the field. First, the technology circumvents the need for training personnel in how to plate, grow and count viable cells from colonies on agar plates. It also eliminates nearly all training and maintenance costs associated with most of the other methods. Second, the invention substantially decreases the time needed for cellular (bacteria) quantifications. Under current methodologies, quantification requires from 24 to 72 hours (plate counts and enrichment cultures), while the present invention permits more accurate quantitation in less than 20 minutes. Third, the technology offers substantial cost savings over existing methods of cellular quantitation.

DISCLOSURE OF INVENTION

Briefly, the present invention describes methods and kits for quantifying viable cells in a sample using fluorescent dyes that can be actively internalized by viable cells and have fluorescence properties measurably altered when bound to target components.

In one aspect of the present invention, a method for quantifying viable cells in a sample is disclosed, comprising the following steps: (1) contacting a sample with a fluorescent dye, wherein the dye is actively internalized by the cells and has fluorescence properties that are measurably altered when bound to target components; (2) detecting total fluorescence of the sample; and (3) correlating the total fluorescence to the number of cells in the sample. Within certain embodiments, (1) the cells in the sample are bacteria; (2) the fluorescent dye binds to DNA of the viable cells; (3) the sample is treated with DNase before it is mixed with the fluorescent dye; (4) the sample is treated with an agent that affects a cell membrane property of the cells (e.g., a detergent) prior to, subsequently or concurrently with the fluorescent dye; or (5) the fluorescent dye is PicoGreen™.

In another aspect of the present invention, a method for measuring the number of live bacteria in a sample with a fluorescent dye is disclosed. The fluorescent dye used needs to be actively internalized by the bacteria and bind to DNA or other specific cellular components. When so bound, the fluorescence properties of the dye are measurably altered. The disclosed method comprises the following steps: (1) adding the fluorescent dye to a fraction of known volume of the sample; (2) measuring the total fluorescence and fluorescence properties of the fraction of the sample; and (3) correlating the total fluorescence to the number of bacteria in the fraction of the sample. Within certain embodiments, the fraction of the sample is treated with DNase or an agent that affects a cell membrane property of the cells (e.g., a detergent) before it is mixed with the fluorescent dye. Within other embodiments, PicoGreen™ is used as the fluorescent dye.

The present invention also discloses kits for quantifying viable cells. One such kit comprises a cell suspension solution, a fluorescent dye that can be actively internalized by viable cells, and instruction for detecting dye binding to cellular components and correlating the binding to colony forming units. The cell suspension solution may include a DNase or an agent that affects cell membrane property, such as a detergent. In certain embodiments, the fluorescent dye may be PicoGreen™ (Molecular Probes, OR). Another kit for quantifying viable cells in a sample comprises a first solution, means for mixing the first solution with the sample, means for concentrating the cells, a second solution containing a fluorescent dye that can be actively internalized by the viable cells and binds to DNA or other specific cellular components, means for mixing the second solution with concentrated cells, means for illuminating the resulting mixture with excitation light, measuring fluorescence emitted, and thereby determining the amount of DNA or other bacterial cellular components that the fluorescent dye binds to, and thereby providing a fluorescence value proportional to the number of bacteria in the sample. Upon binding, the fluorescence properties of the fluorescent dye are altered to a measurable degree. The first solution may contain a DNase or an agent that affects a bacterial cell membrane property, such as a detergent. Within certain embodiments, the fluorescent dye may be PicoGreen™.

A method for measuring the ratio of viable cells to dead cells in a sample is also disclosed. The method may contain the following steps: saturating the sample with an internalizing first fluorescent dye, adding to the sample a second fluorescent dye that has an emission wavelength overlapped with that of the first fluorescent dye and is actively internalized by the viable cells, and detecting the fluorescence quenching of the first fluorescent dye. Either the first fluorescent dye or the second fluorescent dye may be PicoGreen™ in certain embodiments.

DETAILED DESCRIPTION OF DRAWINGS

FIG. 1 is a correlation of relative intensities of the fluorescent emission (TBAK readings) to the standard plate counts (colony forming units/ml) of Mesophilic Bacteria.

DETAILED DESCRIPTION OF THE INVENTION

Figure 2:
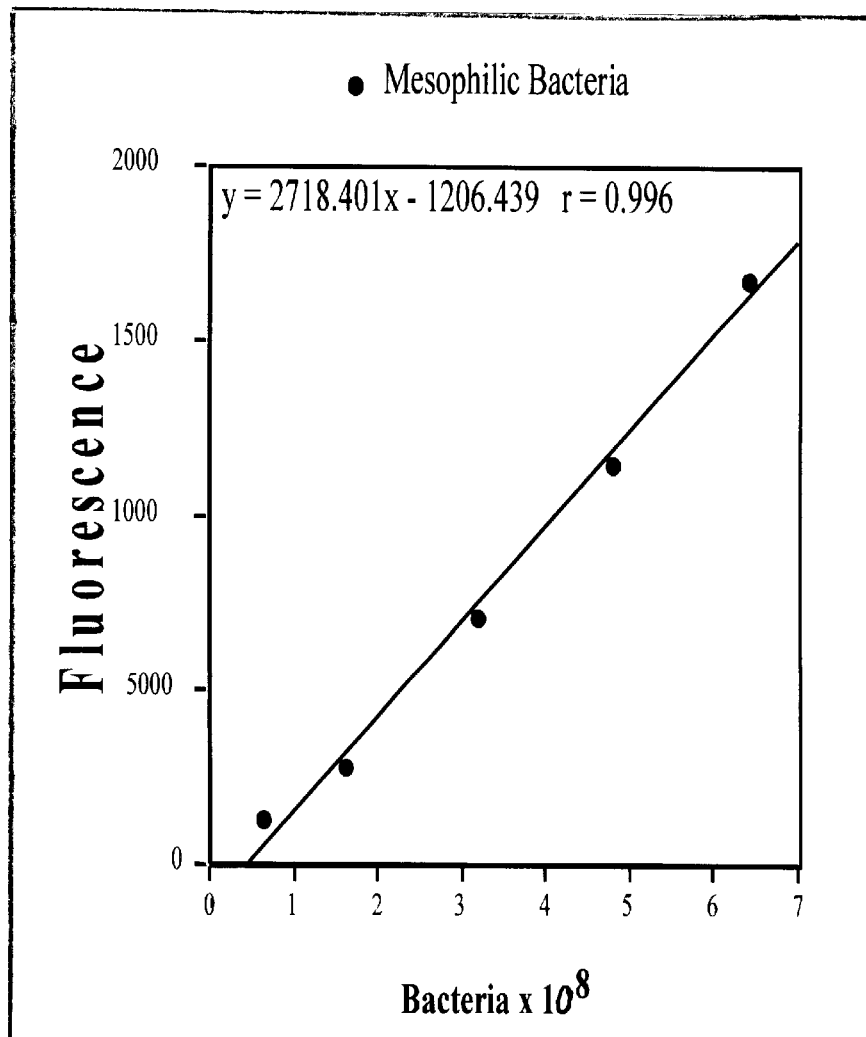
FIG. 2 is a chart that correlates relative fluorescence readings with colony forming units/ml of Mesophilic Bacteria.

As noted above, the subject invention is concerned with methods and kits for quantifying viable cells in a sample. The invention is applicable to the enumeration of all types of viable cells, including eukaryotes, such as plant and animal cells (e.g., mammalian cells, particularly human cells), and prokaryotes, particularly bacteria (including both Gram-positive and Gram-negative bacteria), yeast and other fungi. Viable cells are cells that have intact cell membranes and are metabolically active.

As those of ordinary skill in the art readily appreciate, the sample in which viable cells need to be quantified can be from any source. Typically, the sample is a bodily fluid such as blood, urine, spinal fluid, or other similar fluids. Alternatively, the sample is a fermentation medium such as from a biological reactor or food fermentation process such as brewing. The sample may also be food products such as milk, yogurt, cheese, meats, beverages and other foods. Other sources for samples include water, small amounts of solids, or liquid growth medium.

The present invention requires that fluorescent dyes be actively internalized by viable cells in a sample and bind to their target cellular components. In addition, the invention requires that upon binding, the fluorescence properties of the dyes be altered to a measurable degree. The term "actively internalized" refers to fluorescent dyes that penetrate predominantly viable cells through a process other than passive diffusion across cell membranes. It includes, but is not limited to, internalization of fluorescent dyes through receptors on cell surfaces or through channels in cell membranes. As used herein, the term "actively internalized" may be interchangeably referred to as "internalized predominantly."

The target cellular components to which fluorescent dyes bind may be nucleic acids, actin, tubulin, nucleotide-binding proteins, and membrane components. Fluorescent dyes that fluoresce when metabolized by the cells in a sample, such as dequalinium acteate, fluorescein diacetate, or other similar compounds, are also included in the invention.

Examples of fluorescent dyes that bind nucleic acids and suitable for the present invention include, but is not limited to, acridine orange (U.S. Pat. No. 4,190,328), calcein-AM (U.S. Pat. No. 5,314,805), DAPI, Hoechst 33342, Hoechst 33258, and PicoGreen™, ethidium bromide, propidium iodide and the like. When such fluorescent dyes used to quantify viable cells in a sample, it is preferable there are no more than small differences in the nucleic acid content among the individual cells in the sample. The method works accurately for samples containing predominantly a single species of bacteria or other specific cell types under normal growth conditions, such as in cheese starter cultures. However, variation in DNA content of microbes in axenic or microbial consortia cultures affects quantitative measurements less than the variation affects standard and other methods.

The present invention's counting accuracy may also be affected by such factors as effective penetration of viable cells by the dye (which can be readily calculated for any dye), a low level of background fluorescence relative to the amount of fluorescence of dye bound specifically to DNA or other cellular components, low levels of exogenous DNA in the sample, and so on.

PicoGreen™ is particularly useful to the present invention and is commercially available from Molecular Probes, Eugene, Oreg. It is a cyanine dye with high molar absorptivity and very low intrinsic fluorescence. PicoGreen™ is specific for double strand DNA and produces large fluorescence enhancements (over 1000-fold) upon binding to DNA. Haugland, Richard P., *Handbook of Fluorescent Probes and Research Chemicals*, Molecular Probes, Eugene, Oreg., (1996). However, until the present invention it was not known to be taken up predominantly by viable cells.

Dye preparation is typically carried out by dissolving the dye in an aqueous solvent such as water, a buffer solution, or a water-miscible organic solvent such as dimethylsulfoxide (DMSO), dimethylformamide (DMF), methanol or ethanol. In certain embodiments, it is dissolved at a concentration of greater than about 100-times that used for staining samples. Preferably, the staining solution imposes no or minimal perturbation of cell morphology or physiology.

Before contacting fluorescent dyes, the sample or a fraction of the sample may first be rinsed in a buffer solution and centrifuged, filtered or otherwise concentrated. The initial rinse solutions can be made in aqueous or other polar or semi polar solvents containing various salts between 0.05M and 1.0 M with a final pH of between 3.5 and 11.0 at temperatures between −20 degrees C. and 80 degrees C The solutions may also contain reagents that maximize integrity of viable cells while releasing non-cellular materials into the solutions. Such reagents may include phosphates, neutral, anionic and cationic detergent (e.g., Tween NP and Triton series detergents, SDS, and cetyl-trimethyl ammonium BR, chaotropic salts (e.g., bile salts), organic acids (e.g. citrate), and lipids. In addition, when a fluorescent dye specific for DNA is used, the sample may be treated with a DNase to remove exogenous DNA before it is contacted with the dye.

As noted above, the fluorescent dyes need to be internalized by the cells to be enumerated. In the preferred inventive method, an excess of the dye is used in order to saturate the cellular DNA in the sample. This can be determined by adding an amount known to be enough, or else by adding more and more until fluorescence ceases to increase.

In certain embodiments, after contamination is washed from the cells, an agent that affects cell membrane properties may be used to treat the viable cells to speed the internalization process. Such agents include, but are not limited to, detergent-like compounds, surfactants, or other compounds that affect membrane polarity, fluidity, permeability, potential gradient or other membrane properties. Alternatively, DNA from the viable cells may be first extracted and then contacted with a fluorescent dye specific for DNA.

In the case that a sample is highly translucent, fluorescent dyes may be directly added to the sample and the relative fluorescence is then directly measured.

After being contacted with fluorescent dyes, the sample is excited by a light source capable of producing light at or near the wavelength of maximum absorption of the fluorescent complex, such a laser, an arc lamp, an ultraviolet or visible wavelength emission lamp. Any apparatus or device that can measure the total fluorescence of a sample can be used in this invention including flow cytometers. Typically, a standard flurometer is used because of its relative low cost. The instrumentation for fluorescence detection may be designed for microscopic, surface, internal, solution, and non-suspension sample formats. The total fluorescence measured is then used to calculate the number of viable cells in the sample based on a correlation between total fluorescence and the number of viable cells measured using any prior art method (e.g., standard plate count). The fluorescence may be measured at three or more intervals as the dye is entering the cells, so that the final fluorescence can be predicted in advance of saturation, thereby the time required to obtain a cell count is shortened. One of ordinary skill in the art would readily understand that any lightsource or measurement technique maybe used.

The invention also discloses a method of quantifying the ratio of viable cells to dead cells in a sample. In this embodiment, a sample containing both viable and dead cells is first saturated with an internalizing fluorescent dye. This dye need not be actively internalized by viable cells: It may diffuse into both viable and dead cells. After saturation, a second dye having emission wavelengths overlapping with those of the first dye is added to the mixture of the sample and the first dye. The second dye is capable of being internalized predominately by the viable cells in the sample. The internalization of the second dye quenches the fluorescence emitted by the first dye. The quenching effect of the second dye on the first dye can be used to calculate the ratio of viable cells to dead cells in the sample. PicoGreen™ may be used as either the first dye or the second dye in this method.

The present invention also discloses kits and apparatuses for quantifying viable cells. One such kit comprises a cell suspension solution, a fluorescent dye, and instruction for detecting the binding of the dye to cellular components of the viable cells and correlating the binding to colony forming units. The suspension solutions may be aqueous or other polar or semi-polar solvents containing various salts between 0.05M and 1.0 M with a final pH of between 3.5 and 11.0 at temperatures between −20 degrees C and 80 degrees C. The solutions may also contain reagents that maximize integrity of viable cells while releasing non-cellular materials into the solutions as described above, a DNase, or an agent that affects cell membrane properties, such as a detergent. The fluorescent dye in the kit is capable of being actively internalized by the viable cells, binding to cellular components and altering its emission of fluorescence upon the binding to a measurable degree. The instruction contains necessary information of how to use the kit to quantify viable cells in a sample, such as how to detect the fluorescence emitted from the dye and how to correlate the fluorescence measured with colony forming units.

In another aspect, a kit for quantifying live bacteria in a sample may include any one or combinations of the following: a cell suspension solution, means for mixing the cell suspension solution with the sample, means for concentrating the cells, a fluorescent dye solution, means for mixing the dye solution with concentrated cells, and means for illuminating the resulting mixture with excitation light and measuring fluorescence emitted. The cell suspension solution may be the same as in the other kit described above. Any means for mixing solution with a sample known in the art (e.g., pipets, vortex) can be included in this kit. Any means for concentrating cells from solutions known in the art (e.g., centrifugation, filtration) may also be included in the kit. The fluorescent dye in the kit is capable of being actively internalized by the viable cells, binding to cellular components and altering its emission of fluorescence upon the binding to a measurable degree. Any means for illuminating a fluorescent solution with excitation light and measuring fluorescence emitted known in the art (e.g., flow cytometers, flurometer) may be included in the kit.

Refinements of the above-described kits may include other dyes that bind uniquely to other cellular components of the sample, means for spectral and time-resolved analysis of the emitted fluorescent light, and means for separating the cell components to which the fluorescent dye binds from the sample before contacting with the fluorescent dye.

Depending on the properties of the fluorescent dye, the disclosed methods and kits may also be used in various assays other than viable cell quantification. For instance, the use of fluorescent dyes that is capable of differentiating two kinds of bacteria enables the measurement of the ratio between the two kinds. The use of a fluorescent dye specific for a particular enzymatic activity may also be used to quantify cells using the particular enzymatic activity. For example, fluorescein diacetate may be used to enumerate cells with active esterase. Such a fluorescent dye can be further used to enumerate cells in which a particular enzymatic activity is induced by certain chemicals (e.g., naphthalene and dequalinium acetate for the induction of esterase activity) or treatments (e.g., heat). In addition, fluorescent dyes that differentiate prokaryotes and eukaryotes based on their differences in cell membrane proteins, the presence or absence of certain organelles, and metabolism may be used to quantify prokaryotic cells, eukaryotic cells, or the ratio between the two types of cells. Furthermore, fluorescent dyes of which intensity is enhanced by contacting nucleated or enucleated cells in a sample that are known to be dead or not actively metabolizing in a sample may be used to enumerate such cells.

In other embodiments, fluorescent dyes that quench upon binding to specific cellular components after being predominantly internalized by viable cells may also be used to quantify viable cells. In yet other embodiments, dyes or other substances that change the NMR signature of cells or any other bulk-detectable property of the cells may also be used for enumerating cells.

The present invention provides methods, kits, and apparatuses for simple dye associated quantitation that allows one to inexpensively determine the cell count in a particular sample. One of ordinary skill in the art will readily appreciate that alternatives to the steps herein described for quantitating cells may be used and are encompassed herein. Accordingly, all alternatives will use a kit or method wherein a dye is utilized to stain cells and a detection method. One key aspect of the present invention is its substantial cost savings when utilized in industrial settings as compared to old plate count systems.

All patents, patent applications and references cited herein are incorporated herein in their entirety. Accordingly, incorporated herein by reference are U.S. Pat. Nos.: 5,437,980; 5,563,070; 5,582,984; 5,658,751; 5,436,134; Catt, S. L., Sakkas, D., Bizzaro, D., Bianchi, P. G., Maxwell, W. M. and Evans, G.; (1997) Molecular and Human Reproduction 3:821–825; Ferguson, L. R., and Denny, W. A.; (1995) Mutation Research 329:19–27; and Latt, S. A. and Wohlleb, J. D.; (1975) Chromosoma 52:297–316.

The following examples are offered by way of illustration, and not by way of limitation. All of the references, including patents, patent applications, and journal references are hereby incorporated by reference in their entirety.

EXAMPLES

Example I

Quantitation of Bacterial Cell Number

This example illustrates a method of enumerating live bacterial cells.
Solutions
  Solution A. This is a wash/isolation solution that prepares the cells to take up the dye and permits removal of any interfering exogenous substances. All chemicals are reagent grade and can be obtained from common suppliers in the trade.

Ingredients and Preparation and Storage of Solution A (Ten Times Concentrate)
Ingredients:
  NaCl . . . 80.0 grams
  KCl . . . 2.0 grams
  $Na_2HPO_4$ . . . 14.4 grams
  $KH_2PO_4$ . . . 2.4 grams
  NaOH . . . sufficient to reach pH 7.4
  Pure water . . . sufficient for 1 liter
Preparation:
  The above chemicals are dissolved in 850 ml of pure water at room temperature. The pH is adjusted to 7.4 with 1M NaOH. The volume is adjusted to 1 liter with pure water. The solution is autoclaved and may be stored at room temperature for up to one year.

Ingredients, Preparation and Storage of Stock Solution of Sodium Dodecyl Sulfate
Ingredients:
  Sodium dodecyl sulfate (SDS) . . . 2.0 grams
Preparation:
  Dissolve 2.0 grams of SDS in enough pure water to make a final volume of 100 ml.
Storage:

The solution may be stored for up to one year at room temperature.

Ingredients, Preparation and Storage of Working Solution A

Ingredients:

| | |
|---|---|
| Solution A (Ten Times Concentrate) | 100 ml |
| Stock Solution of SDS | 0.5 ml |
| Pure water | 900 ml |

Preparation:
Add the above solutions to a 1 liter container. Solution A is used in the invention.

Storage:
Solution A is autoclaved and then stored closed at room temperature.

Solution B. This solution contains a dye that stains viable cells. The formulation may allow unique stability and rapid uptake of the dye by the viable cells. All chemicals are reagent grade and can be obtained from common suppliers in the trade such as Sigma Chemical Co., St. Louis, MO.

Ingredients and Preparation and Storage of Solution B

Ingredients:

| | |
|---|---|
| Hoechst 33258 | 100 mg |
| Sterile pure water | 10 ml |
| Propylparaben | 0.1 ml |
| | (approximately-- this amount is not critical) |

Preparation of Solution B One Hundred Times Concentrate (an example using Hoechst 33258):

Solution B is made by dissolving Hoechst 33258 or similar dye in sterile pure water to a final concentration of 10 ug/ml. An antioxidant such as propyl gallate or propylparaben is added to increase shelf life of the solution.

Storage:
This solution is stored in the dark at 4 degrees C. It is stable for at least 6 months.

Dilution of Solution B

Ingredients:

| | |
|---|---|
| Solution B (One Hundred Times Concentrate) | 0.1 ml |
| Sterile, pure water | 9.9 ml |

Dilution:
Solution B (One Hundred Times Concentrate) is diluted 1/100 in sterile, pure water. For example, 100 ml of Solution B one Hundred Times Concentrate is dissolved into 9.90 ml of sterile, pure water for a final concentration of 0.1 mg.ml.

Methods

The procedure given below discloses an example of a method for quantitating bacteria present in a liquid suspension using the invention.

1. Calibration and Blanking of the Fluorometer.

A simple table-top fluorometer such as Turner Designs model 360 is used which is fitted with a set of filters, 365 nm excitation light wavelength and 460 nm emission light wavelength. A calibration solution of known fluorescence intensity is employed to calibrate the instrument to a reading of zero. A blank solution such as Solution A is used to set the instrument to a reading of zero. All procedures are carried out at room temperature.

Blanking Procedure:
 a) place blank standard solution in reader (fluorometer) cuvette
 b) close lid of fluorometer and push "blank" on keypad
 c) adjust the fluorometer to read 5000 relative fluorescent units Calibration Procedure:
 a) place unique "calibration solution" in cuvette
 b) close lid of fluorometer and push "calibration" on keypad
 c) adjust the fluorometer to read 5000 relative fluorescent units 2. Method for Counting Bacteria
 a) Add 200 microliters of Solution A to the cuvette containing bacterial cells.
 b) Add a 5 microliter volume of bacterial cells to Solution A in the cuvette.
 c) Centrifuge at 2000 g for 30 seconds.
 d) Remove the supernatant solution by shaking or pipetting to remove it while retaining the cells.
 e) Add 200 microliters of Solution A to the cuvette containing bacteria and vortex to suspend the cells.
 f) Centrifuge at 2000 g for 30 seconds.
 g) Remove the supernatant solution by shaking or pipetting, while retaining the cells.
 h) Add 100 microliters of Solution B, vortex to suspend the cells and incubate for 10 min at room temperature.
 i) Place cuvette in fluorometer, close the lid and record the relative fluorescence value.
 j) Correlate the relative fluorescence reading with colony forming units/ml.

Data

FIG. 1 is an example of a correlation of relative intensities of fluorescence emission (TBAK readings) to the standard plate counts (colony forming units/ml). FIG. 2 is another example of correlation of relative fluorescence readings with colony forming units/ml in a chart form. Both figures indicate that the intensity of the fluorescence emission is directly proportional to the cell numbers as measured by the standard plate count method.

What is claimed is:

1. A kit for quantifying viable cells, comprising: a first container containing a first solution, means for mixing said first solution with a sample containing an unknown number of viable cells, means for concentrating the solids and cells from the mixture of said first solution with said sample and retaining said solids from the remainder of said mixture, a second solution containing a fluorescent dye that is actively internalized by the viable cells and binds selectively to double-stranded DNA or other specific cellular components, whereupon binding its target the dye's fluorescence is altered, indicating viable cells in the sample, means for mixing said second solution with said solids to form a second mixture, and means for illuminating the mixture of said second solution with said solids with excitation light and measuring fluorescence emitted by said mixture, and thereby determining the amount of DNA or other unique cell component in viable bacteria in said sample, and providing thereby a fluorescence value proportional to the number of viable cells in said sample.

2. The kit of claim 1 wherein the first solution comprises a DNAase.

3. The kit of claim 1 wherein the first solution comprises a detergent.

4. The kit of any one of claims 1, 2, or 3, wherein the fluorescent dye in said second solution is a cyanine dye.

* * * * *